(12) United States Patent
Iwamatsu et al.

(10) Patent No.: US 8,409,507 B2
(45) Date of Patent: Apr. 2, 2013

(54) AUTOMATIC ANALYZER

(75) Inventors: Hirokazu Iwamatsu, Hitachinaka (JP);
Kazuhiro Nakamura, Naka (JP);
Satoshi Shibuya, Hitachinaka (JP);
Yasunao Awata, Yokohama (JP);
Hidetoshi Sugiyama, Hitachinaka (JP);
Werner Doppen, Eberfing (DE);
Dietmar Kappelhoff, Goldau (CH)

(73) Assignees: Hitachi High-Technologies Corporation, Tokyo (JP); Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/056,740

(22) Filed: Mar. 27, 2008

(65) Prior Publication Data

US 2008/0240989 A1    Oct. 2, 2008

(30) Foreign Application Priority Data

Mar. 30, 2007    (JP) ................. 2007-090125

(51) Int. Cl.
*G01N 21/00* (2006.01)
*G01N 31/00* (2006.01)
*G01N 33/00* (2006.01)
*G01N 15/06* (2006.01)
*G01N 33/48* (2006.01)

(52) U.S. Cl. ......................................... 422/67; 422/68.1
(58) Field of Classification Search .................... 422/67, 422/68.1

See application file for complete search history.

(56) References Cited

U.S. PATENT DOCUMENTS

| | | | |
|---|---|---|---|
| 6,413,475 B2 * | 7/2002 | Ishizawa et al. | 422/106 |
| 6,737,021 B2 * | 5/2004 | Watari et al. | 422/63 |
| 2004/0101440 A1 * | 5/2004 | Ishizawa et al. | 422/64 |
| 2005/0175503 A1 * | 8/2005 | Shiba et al. | 422/64 |
| 2005/0220671 A1 * | 10/2005 | Stein et al. | 422/67 |

FOREIGN PATENT DOCUMENTS

| | | |
|---|---|---|
| EP | 0845674 B | 3/2002 |
| JE | 2004-317321 A | 11/2004 |
| JP | 6-66813 A | 3/1994 |
| JP | 10-142230 | 5/1998 |
| JP | 3597958 | 9/2004 |
| JP | 2006-275962 A | 10/2006 |

* cited by examiner

*Primary Examiner* — In Suk Bullock
*Assistant Examiner* — Bryan Kilpatrick
(74) *Attorney, Agent, or Firm* — Mattingly & Malur, PC

(57) ABSTRACT

An automatic analyzer includes a status table storing the status of each analysis module and reagent information identifying each reagent, the supply of which is exhausted, and allowing tracking of the status of each analysis module, etc. The automatic analyzer determines, based on the status table, whether and how it can continue current analysis, and stores the determination results in its instruction information table. The instruction information table stores analysis-unit or -module operating information and information to be supplied to the user or operator. The analysis-unit operating information includes instructions for the analysis modules to initiate an analysis in a normal manner, finish an analysis in a normal manner, omit a pre-analysis operation, omit a post-analysis operation, or stop sampling, etc. Further, the reagent information and the analysis module status are updated each time a reagent container is replaced by the operator.

5 Claims, 5 Drawing Sheets

AUTOMATIC ANALYZER

BACKGROUND OF THE INVENTION

1. Field of the Invention

The present invention relates to an automatic analyzer for qualitatively and quantitatively analyzing biological samples such as blood or urine samples, and more particularly to an automatic analyzer employing a means for detecting the remaining amount of each reagent.

2. Description of the Related Art

Conventional automatic analyzing apparatus has been designed to perform its analysis operation in such a manner that if the amount of any one of the essential reagents in respective containers (e.g., bottles) falls to zero, the apparatus is set to a standby state to allow replacement of the empty container with a full one. It is common for the automatic analyzing apparatus to have the capability to notify the operator of exhaustion of the supply of a reagent by graphically indicating it on the display of the operation unit. In response to this indication, the operator replenishes the exhausted supply of the reagent (e.g., replaces the reagent container, etc.) after making sure that each analysis module using the reagent has completed the analysis of its current specimen sample. The operator then causes the automatic analyzing apparatus (and hence each analysis module) to resume its analysis operation after making sure that the supply of the reagent has been restored. This means that the operator needs to monitor a plurality of display screens to check the operating sate of the apparatus during the time between the reagent supply exhaustion and the resumption of the analysis operation. Furthermore, each analysis module must perform a post-analysis operation after completing the analysis of its current specimen sample and also must perform a pre-analysis operation before resuming its analysis operation. That is, exhaustion of the supply of a reagent causes the automatic analyzing apparatus to stay in a standby state for a long time before resuming its analysis operation. Japanese Patent No. 3597958 discloses an automatic analyzer having an interrupt button for reagent bottle replacement which is pressed by the operator to set the analyzer in a standby state when it is necessary to replace a reagent bottle with a new one. The automatic analyzer uses a lamp, etc. to notify the operator when it is in the standby state.

SUMMARY OF THE INVENTION

The automatic analyzer of the above patent publication is disadvantageous in that the operator must determine whether the supply of any one of the reagents is exhausted and, if so, determine whether to replace its bottle. Therefore, it might happen that the operator causes the apparatus to start an analysis operation without checking the screen for the remaining amount of each reagent (or the supply of each reagent).

It is, therefore, an object of the present invention to provide an easy-to-use automatic analyzer which is designed such that when the supply of one of the reagents has been exhausted, the analyzer automatically determines whether each analysis module has completed the analysis of its current specimen sample and, if so, notifies the operator of the fact that the exhausted supply can be replenished (e.g., the empty reagent container, etc. can be replaced). This automatic analyzer is also designed such that it automatically resumes its analysis operation after the exhausted supply has been replenished.

The automatic analyzer of the present invention includes a status table for storing the status of each analysis module. (The status of each analysis module varies during the analysis operation of the module.) Specifically, the status table is designed to store the status of each analysis module and reagent information, thereby allowing identification of each reagent the supply of which is exhausted and allowing tracking of the status of each analysis module, etc. The automatic analyzer determines, based on the status table, whether and how it can continue its current analysis operation. The analyzer stores the results of this determination in its instruction information table. More specifically, the instruction information table stores analysis-unit operating information (or analysis-module operating information) and information to be supplied to the user or operator. The analysis-unit operating information includes instructions which instruct the analysis modules to initiate an analysis in a normal manner, finish an analysis in a normal manner, omit a pre-analysis operation, or omit a post-analysis operation. The analysis-unit operating information also includes an instruction which instructs that when the supply of one of the reagents has been exhausted, the analysis modules using that reagent should stop sampling and each analysis module should finish the analysis of its current specimen sample without performing a post-analysis operation. Further, the reagent information and the status of each analysis module in the status table are updated each time a reagent container is replaced by the operator. This allows the automatic analyzer to generate, based on the status table, information for graphically indicating on its operation unit the completion of replacement of each reagent container. When the analyzer generates such information, it also generates and stores analysis-unit operating information which instructs the analysis modules to initiate an analysis without performing a pre-analysis operation.

Thus, when the supply of a reagent in its reagent compartment has been exhausted, the automatic analyzer notifies the operator of when the exhausted supply can be replenished (i.e., when the empty reagent container can be replaced), thereby making it easy for the operator to determine the replacement timing of each reagent container. After the completion of replacement of the empty reagent container, the automatic analyzer automatically resumes its analysis operation, without any manipulation by the operator. In such a case, each analysis module does not perform a post-analysis operation after finishing its current analysis and also does not perform a pre-analysis operation before initiating an analysis after replacement of the empty container, thereby reducing the time required for the automatic analyzer to resume its analysis operation, as compared to conventional arrangements.

DETAILED DESCRIPTION OF THE EMBODIMENTS

An embodiment of the present invention will now be described with reference to the accompanying drawings.

Figure 1:
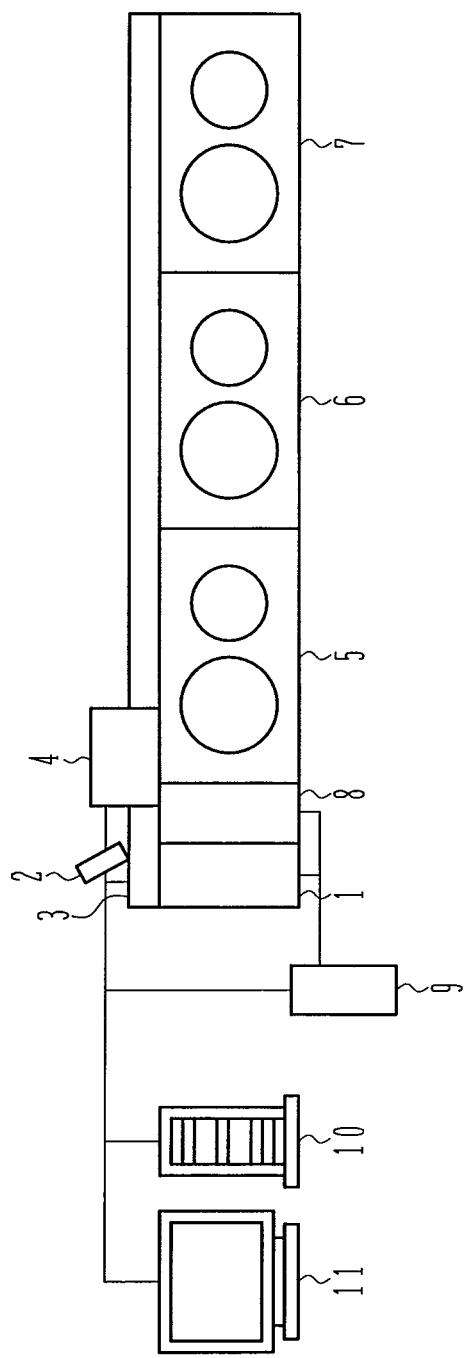
FIG. 1 is a schematic diagram showing the overall configuration of an automatic analyzer according to an embodiment of the present invention.

FIG. 1 is a schematic diagram showing the overall configuration of an automatic analyzer according to an embodiment of the present invention.

This automatic analyzer includes a rack feeding unit 1, an ID reader 2, a conveying mechanism 3, a temporary rack storage unit 4, analysis modules 5, 6, and 7, a rack retrieving unit 8, and an overall control computer 9.

The rack feeding unit 1 supplies a plurality of racks at one time. The automatic analyzer may include any number of analysis modules although the present embodiment assumes that there are only three analysis modules.

The conveying mechanism 3 receives racks from the rack feeding unit 1 and transfers them to the analysis modules 5, 6, and 7, the temporary rack storage unit 4, or the rack retrieving unit 8.

The rack feeding unit 1 is provided with the overall control computer 9, which controls the rack feeding unit 1, the ID reader 2, the conveying mechanism 3, the temporary rack storage unit 4, and the rack retrieving unit 8. Further, an operation unit 10 and a display unit 11 are connected to the overall control computer 9 to store information and to display analysis results, respectively.

Each specimen tube held in each rack bears a specimen ID, i.e., attribute information of the specimen therein (including the serial number, the name of the patient, the requested analysis items, etc.), and each rack bears a rack ID, or rack identification information (including the rack number, etc.). Each rack placed in the rack feeding unit 1 is conveyed by the conveying mechanism 3. At that time, the rack ID and the specimen ID of each specimen tube in the rack are read by the ID reader 2, and the read data (attribute information) is sent to the overall control computer 9 which then determines, based on the read attribute information, which analysis module is to be used to analyze each specimen.

Figure 2:
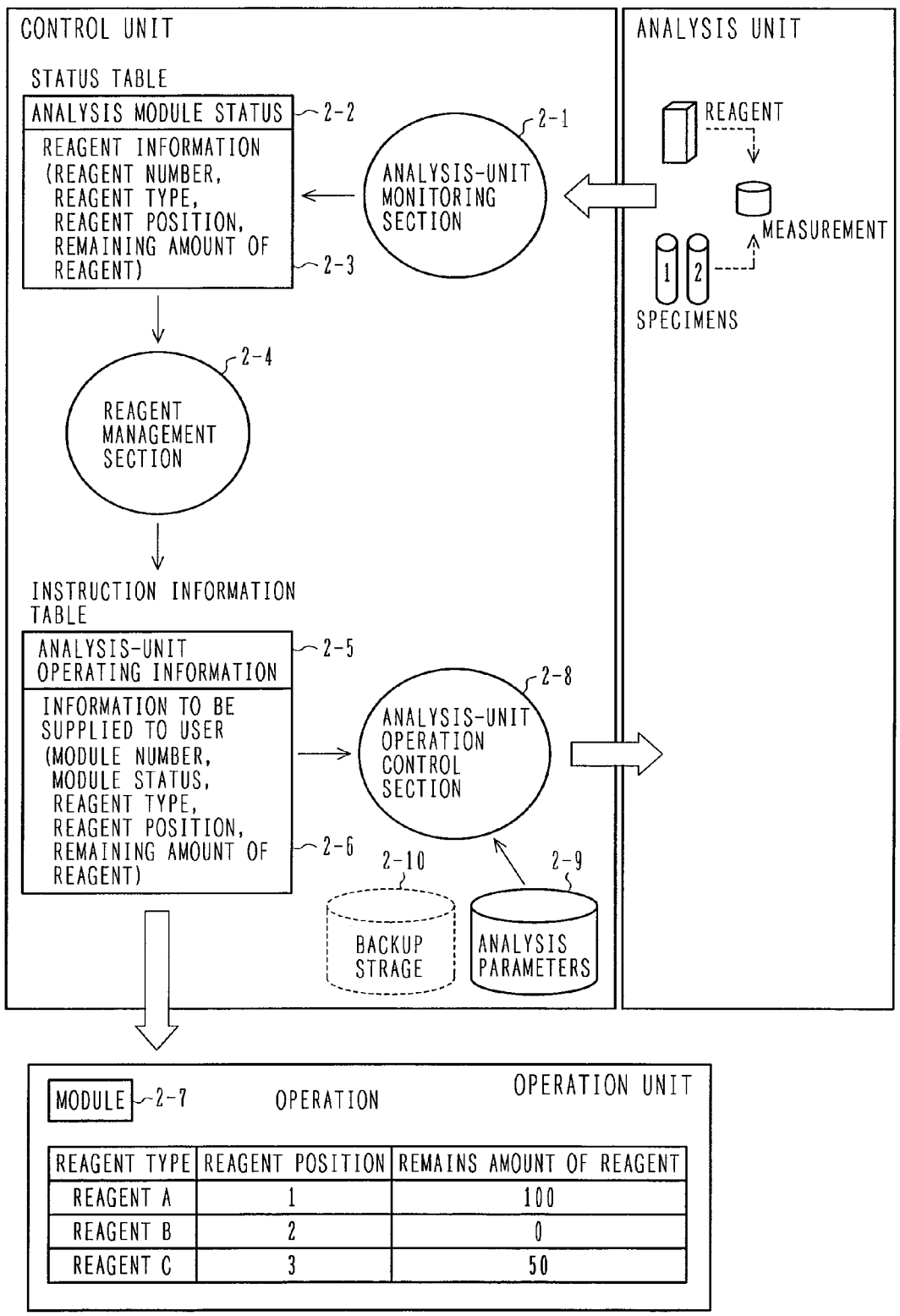
FIG. 2 is a diagram illustrating the overall operation of the automatic analyzer.

FIG. 2 is a diagram illustrating the overall operation of the automatic analyzer of the present invention.

In FIG. 2, the analysis modules, etc. are collectively referred to as the "analysis unit." It should be also noted that the overall control computer 9 implements a control unit which includes an analysis-unit monitoring section 2-1, a reagent management section 2-4, and an analysis-unit operation control section 2-8, as shown in FIG. 2. The analysis-unit monitoring section 2-1 stores in a status table the module status 2-2 of each analysis module and reagent information 2-3. (The module status 2-2 of each analysis module varies during the analysis operation of the module.)

The reagent management section 2-4 updates analysis-unit operating information 2-5 and information 2-6 to be supplied to the operator or user based on the module status 2-2 of each analysis module and the reagent information 2-3. When one of the reagent containers has become empty, the reagent management section 2-4 notifies the operator of when the empty container can be replaced by displaying a graphical indication 2-7 on the operation unit 10.

The analysis-unit operation control section 2-8 sends to each analysis module an operation instruction instructing the module to stop sampling, finish its current analysis, or initiate an analysis, etc. as necessary. The analysis-unit operation control section 2-8 also sends analysis parameters 2-9 to each analysis module before the section 2-8 instructs the module to initiate an analysis. Further, the analysis-unit operation control section 2-8 stores the analysis parameters in a backup storage 2-10 when instructing the analysis module to finish its current analysis without performing a post-analysis operation.

Figure 3:
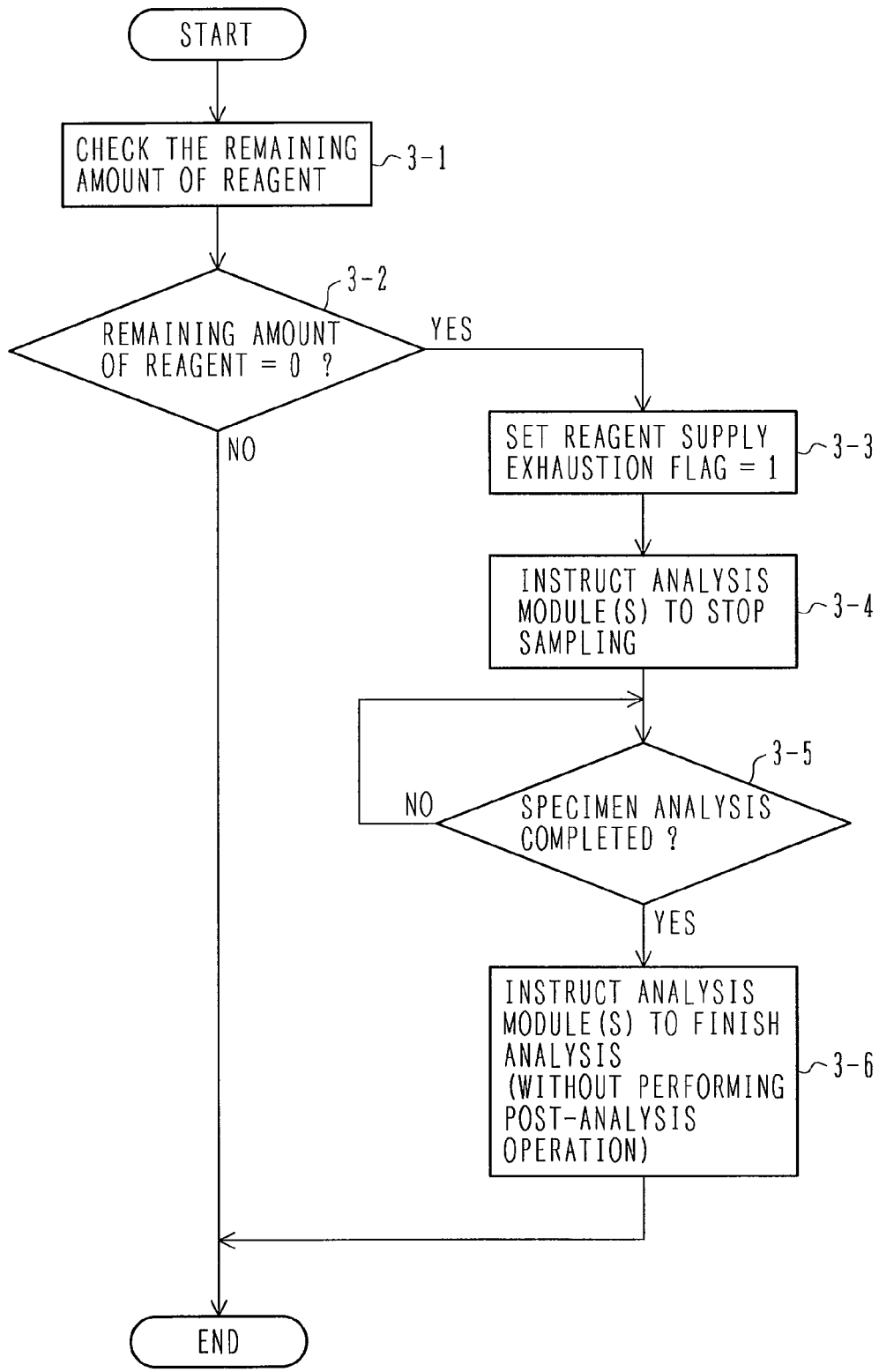
FIG. 3 is a flowchart illustrating the control sequence for causing analysis modules of the automatic analyzer to stop sampling and finish their current analysis when the supply of one of the reagents is exhausted.

FIG. 3 is a flowchart illustrating the control sequence for causing analysis modules of the automatic analyzer to stop sampling and finish their current analysis when the supply of one of the reagents is exhausted. At step 3-1, the control unit receives information on the remaining amounts of the reagents used for specimen analysis from the analysis unit. The control unit then determines at step 3-2 whether or not the supply of any one of the reagents is exhausted. If the supply of none of the reagents is used up, the processing ends. If, on the other hand, the supply of one of the reagents is exhausted, the control unit sets the reagent supply exhaustion flag to 1 at step 3-3. (The control unit first checks this flag when determining whether to instruct each analysis module to automatically initiate an analysis without performing a pre-analysis operation.) At step 3-4, the control unit instructs that the analysis modules using the reagent the supply of which is exhausted should stop sampling. The control unit then waits for each analysis module to complete the analysis of its current specimen sample, at step 3-5. Upon completion of the analysis, the control unit instructs each analysis module to interrupt its analysis operation without performing a post-analysis operation (i.e., cleaning of the probe, discarding of the reaction cup, etc.).

Figure 4:
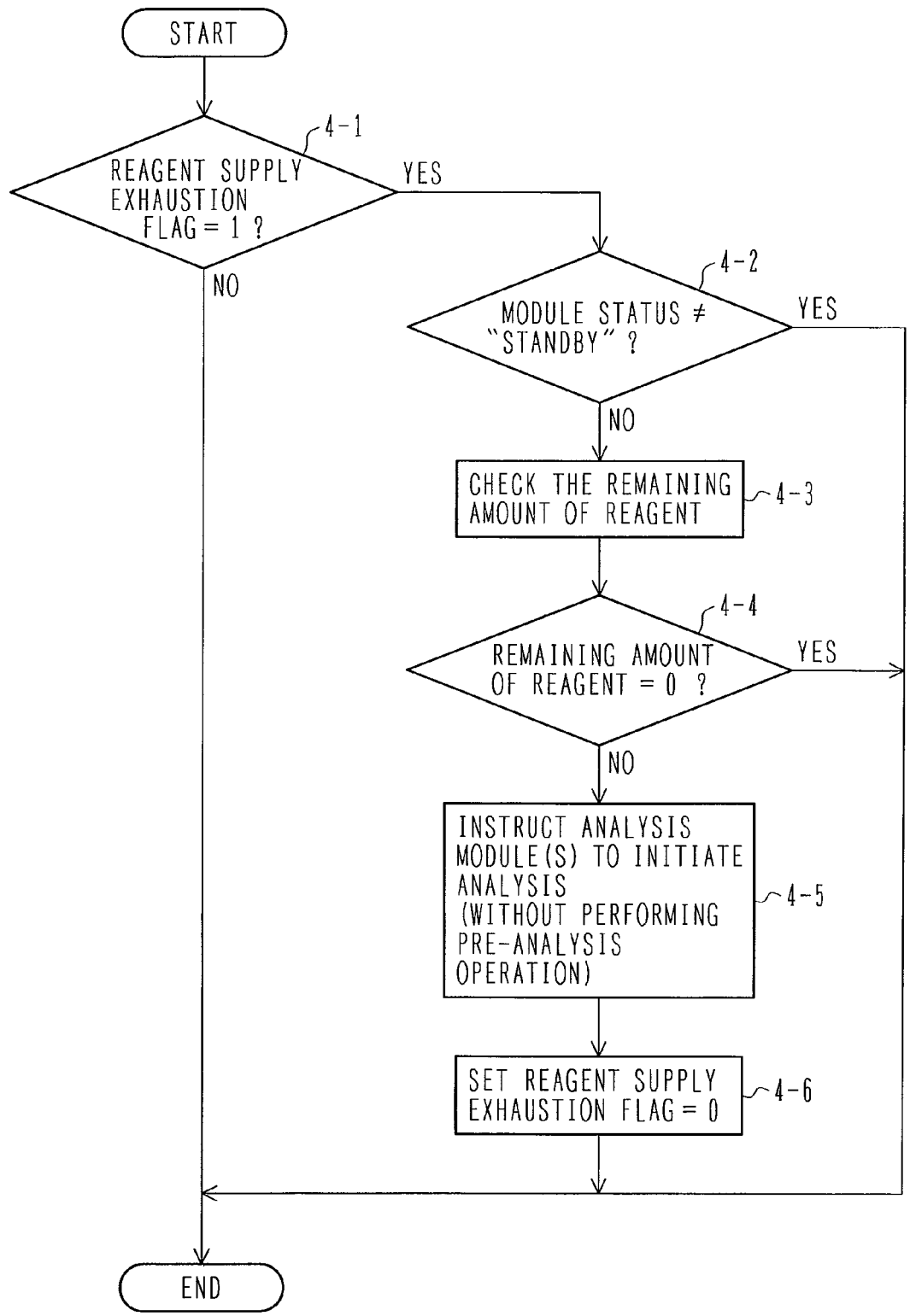
FIG. 4 is a flowchart illustrating the control sequence for causing the analysis modules to automatically resume their analysis operation after the exhausted supply is replenished.

FIG. 4 is a flowchart illustrating the control sequence for causing the analysis modules to automatically resume their analysis operation after the exhausted supply is replenished (e.g., after the empty reagent container is replaced). The control unit initiates this control sequence when the analysis modules have assumed a standby state after the exhausted supply of the reagent had been replenished. At step 4-1, the control unit determines whether the reagent supply depletion flag is set to 0 or 1. If the reagent supply depletion flag is set to 0, the processing ends. If, on the other hand, the flag is set to 1, the control unit determines whether the status of each analysis module is Standby at step 4-2. If not, the processing ends. If the status of each analysis module is Standby, the control unit obtains information on the remaining amount of each reagent at step 4-3 and determines at step 4-4 whether the supply of any one of the reagents is exhausted. If so, the processing ends. If the supply of none of the reagents is exhausted, at step 4-5, the control unit instructs each analysis module to initiate an analysis without performing a pre-analysis operation (i.e., cleaning of the probe, discarding of the reaction cup, etc.). Then, at step 4-6, the control unit sets the reagent supply depletion flag to 0, and the processing ends.

Figure 5:
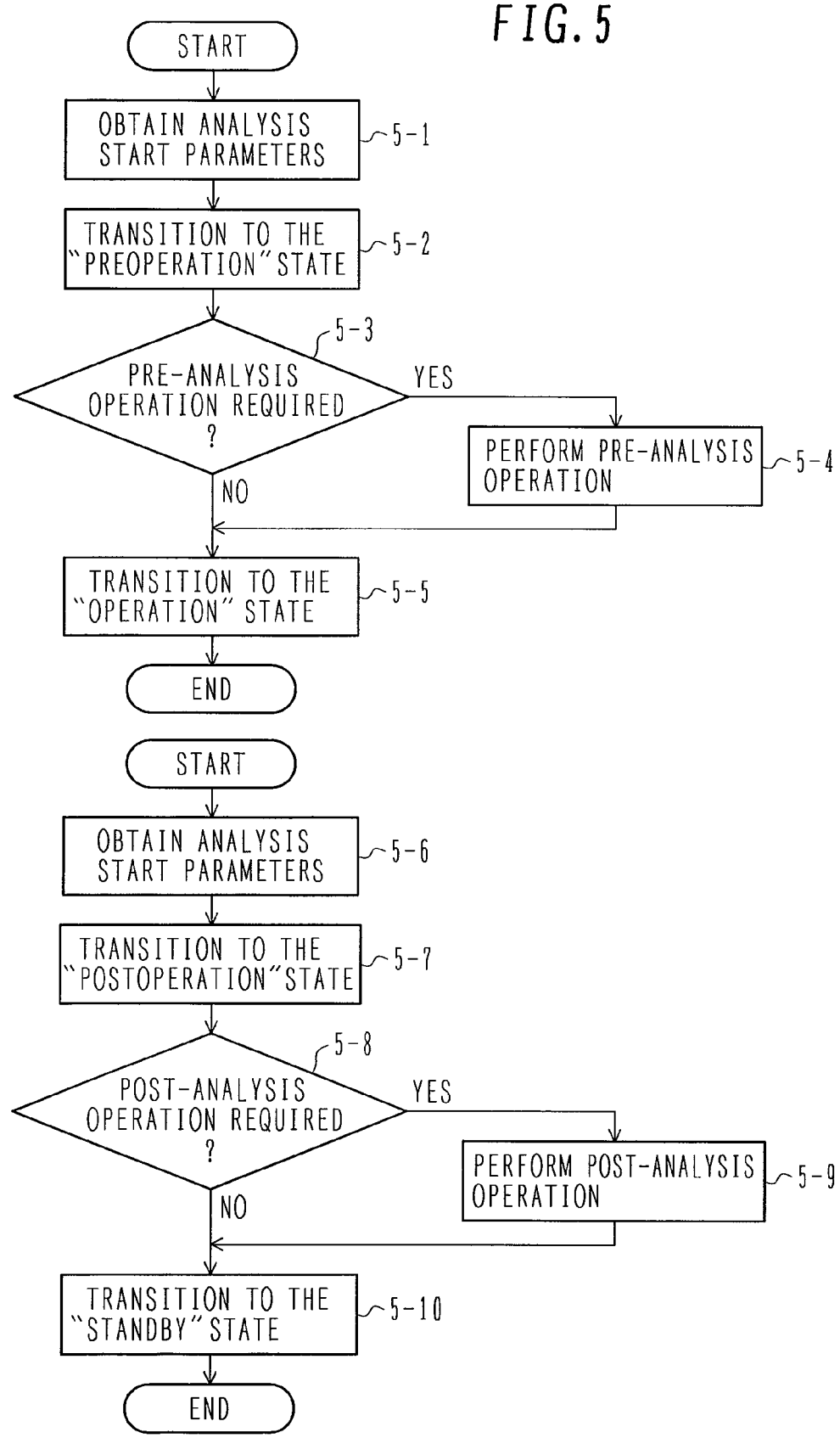
FIG. 5 includes flowcharts illustrating the manner in which the automatic analyzer determines whether to perform a pre-analysis operation when initiating an analysis and the manner in which the analyzer determines whether to perform a post-analysis operation when finishing an analysis.

FIG. 5 includes flowcharts illustrating the manner in which the automatic analyzer determines whether to perform a pre-analysis operation when initiating an analysis and the manner in which the analyzer determines whether to perform a post-analysis operation when finishing an analysis. Specifically, the analyzer performs the following steps before initiating an analysis. The control unit obtains analysis start parameters at step 5-1 and causes the automatic analyzer to transition to the PreOperation state (a standby state) at step 5-2. At step 5-3, the control unit determines whether a pre-analysis operation should be performed. If not, at step 5-5, the analyzer transitions to the Operation state (an operating state) without performing the pre-analysis operation. The analyzer is ready to analyze specimens after step 5-5. If it is determined at step 5-3 that the pre-analysis operation should be performed, the processing proceeds to step 5-4 where the pre-analysis operation is performed. On the other hand, the analyzer performs the following steps after completing an analysis. The control unit obtains analysis end parameters at step 5-6 and causes the analyzer to transition to the PostOperation state (an operating state) at step 5-7. At step 5-8, the control unit determines whether a post-analysis operation should be performed. If not, at step 5-10, the analyzer transitions to the Standby state (a standby state) without performing the post-analysis operation. If it is determined at step 5-8 that the post-analysis operation should be performed, the processing proceeds to step 5-9 where the post-analysis operation is performed.

What is claimed is:

1. An automatic analyzer comprising:
    reagent amount detecting means for detecting the remaining amount of a reagent; and
    control means configured to perform control such that when said reagent amount detecting means has detected that the remaining amount of any one of a plurality of reagents has fallen to a predetermined threshold value or less, an analysis device using that reagent stops specimen sampling and assumes a standby state after finishing an analysis of its current specimen sample,
    wherein, when the reagent amount detecting means has detected that the remaining amount of any one of the reagents has fallen to a predetermined threshold value or less, the control means is configured to perform a first step of control where an analysis device using that reagent stops specimen sampling and assumes a standby state from an operation state after finishing an analysis of a current specimen sample, and to perform second step of control where a part of processing including one of probe washing and reaction cup abandonment performed before the analysis device has changed to the standby state from the operation state is omitted, and
    wherein, when the reagent for which said reagent amount detecting means has detected that the remaining amount has fallen to a predetermined threshold value or less has been replenished such that the amount of the reagent exceeds the predetermined threshold value, said control means is configured to perform a third step of control where, when said analysis device changes to the operation state from the standby state, a part of processing including one of probe washing and reaction cup abandonment performed before the analysis device changes to the operation state from the standby state is omitted.

2. An automatic analyzer according to claim 1,
    wherein the control means is configured to indicate that said analysis device using said reagent that has fallen to a predetermined threshold value or less is in said standby state.

3. The automatic analyzer as claimed in claim 2, further comprising display means configured to indicate that said analysis device using said reagent that has fallen to a predetermined threshold value or less is in said standby state.

4. The automatic analyzer as claimed in claim 3, wherein, when said reagent amount detecting means has detected that the remaining amount of said reagent has exceeded said predetermined threshold value, the control means is configured to perform an additional step of control where said analysis device using said reagent transitions from said standby state to an operating state.

5. The automatic analyzer as claimed in claim 4, wherein the control means is configured to control said analysis device using said reagent as said analysis device transitions from said standby state to said operating state without performing part of a normal post-analysis operation or a normal pre-analysis operation or both.

* * * * *